(12) United States Patent
Latoga et al.

(10) Patent No.: US 6,329,330 B1
(45) Date of Patent: *Dec. 11, 2001

(54) PHOTOSTABLE COMPOSITIONS

(75) Inventors: Gerard A. Latoga; Kennie U. Dee, both of Manila (PH)

(73) Assignee: Johnson & Johnson Consumer Companies, Inc, Skillman, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/088,465

(22) Filed: Jun. 1, 1998

(51) Int. Cl.$^7$ .................. C11D 9/50; C11D 9/60
(52) U.S. Cl. .................. 510/131; 510/130; 510/133; 510/141; 510/147; 510/152; 510/483; 510/391; 510/394
(58) Field of Search .......... 424/401, 59, 70.1, 424/60, 70.16, 65; 514/844; 510/130, 131, 133, 137, 138, 141, 147, 152, 153, 155, 158, 483, 394, 391

(56) References Cited

U.S. PATENT DOCUMENTS

| | | |
|---|---|---|
| 2,921,907 | 1/1960 | Kleyn et al. . |
| 3,793,214 | 2/1974 | O'Neill et al. . |
| 4,469,338 | 9/1984 | Legris . |
| 4,847,072 * | 7/1989 | Bisset et al. .......... 424/59 |
| 4,975,218 * | 12/1990 | Rosser .................. 252/117 |
| 5,439,954 * | 8/1995 | Bush .................... 424/59 |

FOREIGN PATENT DOCUMENTS

| | | |
|---|---|---|
| 0 335 026 B1 | 7/1992 | (EP) . |
| 802447 | 10/1958 | (GB) . |
| 2025 451 | 1/1980 | (GB) . |
| WO 98/00505 | 1/1998 | (WO) . |
| WO 99/05250 | 2/1999 | (WO) . |

OTHER PUBLICATIONS

International Cosmetic Ingredient Dictionary and Handbook—Seventh Edition, 1997, CTFA.*

* cited by examiner

Primary Examiner—Margaret Einsmann
Assistant Examiner—Gregory E. Webb

(57) ABSTRACT

Fatty acid-based compositions which include at least one neutralized fatty acid, a phenol group-containing compound, and a photostable organic ultra-violet absorber are provided. Additionally, a method of preparing such compositions is provided. The method includes neutralizing at least one melted fatty acid; adding an alkanolamine, a phenol group-containing compound, and a photostable organic UV absorber to the neutralized melted fatty acid to form a pourable composition; and cooling the pourable composition.

20 Claims, 5 Drawing Sheets

PHOTOSTABLE COMPOSITIONS

This Application is a continued prosecution application of U.S. application Ser. No. 09/088,465 filed Jan. 19, 2000, which is a continued prosecution application of U.S. application Ser. No. 09/088,465 filed Jun. 1, 1998, both of which are incorporated by reference in their entireties, and claims the benefit thereof.

FIELD OF THE INVENTION

This invention relates to fatty acid-based compositions, and particularly to solid, non-opaque soaps containing phenolic compounds, which are resistant to discoloration by photodegradation.

BACKGROUND OF THE INVENTION

Many materials used in the cosmetics and personal care product industries are unstable in the presence of sunlight. These ingredients are photolabile or ultra violet (UV) labile in that absorbed solar radiation causes degradation of these ingredients. This, in turn, can affect both the activity of the ingredient and the color of products into which these ingredients are incorporated.

This discoloration effect is particularly pronounced when UV-labile materials are dissolved in processing to form transparent or translucent products. Dissolution of such materials is preferred in the production of a transparent or translucent product in order to avoid unsightly specks of the material in the finished product. However, dissolution increases the surface area of the UV-labile material. Generally, the greater the surface area of such material, the greater the rate of photodegradation.

Clear fatty acid-based compositions typically discolor when exposed to sunlight because of the auto-oxidation of fatty acids. This discoloration is accelerated when phenol group-containing compounds, and particularly anti-microbial agents such as Triclosan are present because the alkaline pH of the soap and any polar solvents shift the UV spectrum of the Triclosan. This shift causes the Triclosan to absorb more solar UV energy (290–400$_{nm}$), thereby increasing the rate of discoloration of the soap bar.

Typically, this discoloration effect is not seen in opaque products because it is not necessary to dissolve photolabile materials when preparing an opaque product. Simple physical mixing is sufficient for production of an opaque product.

Antioxidants and metal chelators have been used to combat color degradation due to auto-oxidation. For example, U.S. Pat. No. 4,469,338 describes the use of sodium metabisulfite, sodium sulfite, potassium bisulfite, sodium hydrosulfite, and potassium metabisulfite in combination with citric acid, sodium citrate or potassium citrate in sodium and triethanolamine salts to prevent color degradation. U.S. Pat. No. 3,793,214 describes the direct neutralization of saturated fatty acids with caustic soda and alkanolamine, and European Patent No. 0335026 describes the use of alkanolamine alkalines to achieve and maintain the clarity of transparent soaps. However, results have not been fully satisfactory.

The present inventors have discovered that photostable organic UV-absorbers are effective in maintaining the photostability of fatty acid-based compositions which contain phenol group-containing compounds and particularly in maintaining the clarity of non-opaque soaps containing phenolic compounds.

SUMMARY OF THE INVENTION

Figure 1:
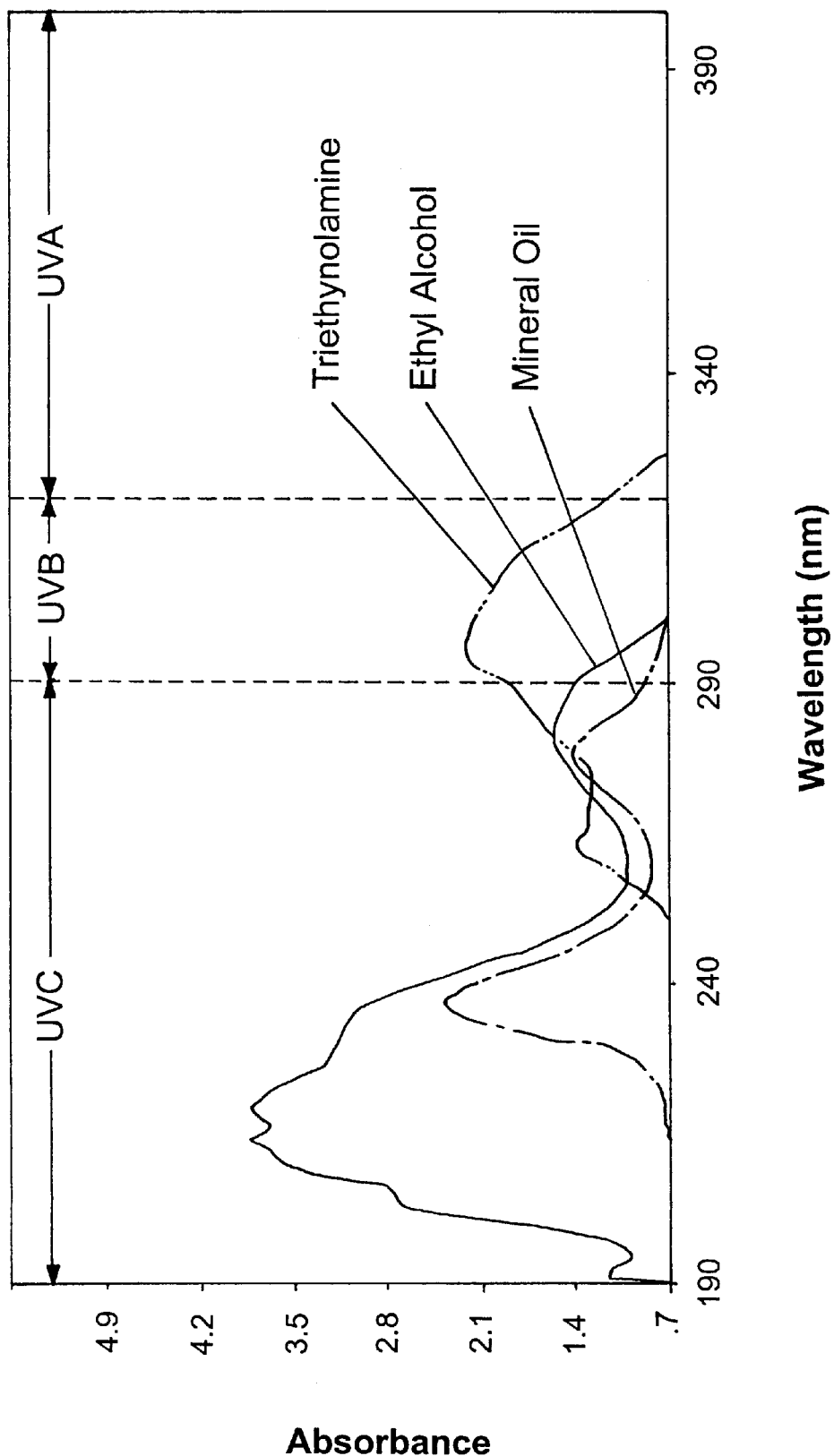
FIG. 1 is a graphic illustration of the UV absorption spectra of 50 ppm Triclosan in triethanolamine, ethyl alcohol, and mineral oil.

According to one embodiment of the present invention, there are provided fatty acid-based compositions which include:

(a) at least one neutralized fatty acid;

(b) a phenol group-containing compound; and (c) a photostable organic ultra-violet absorber; wherein the weight ratio of the UV absorber to the phenol group-containing compound ranges from about 1:10 to about 5:1. Preferably, the compositions are solid, non-opaque anti-microbial soaps.

According to an alternate embodiment of the present invention, there is provided a method of preparing a fatty acid-based composition. The method includes:

(a) neutralizing at least one melted fatty acid;

(b) adding an alkanolamine, a phenol group-containing compound, and a photostable organic UV absorber to the neutralized melted fatty acid to form a pourable composition; and (c) cooling the pourable composition; wherein the weight ratio of said UV absorber to said phenol group-containing compound ranges from about 1:10 to about 5:1. Again, preferred compositions prepared by this method are solid, non-opaque anti-microbial soaps.

DETAILED DESCRIPTION OF THE INVENTION

Preferred compositions of the present invention are soaps and particularly soaps that include a neutralized fatty acid, an anti-microbial agent, and a photostable organic UV absorber. These soaps may be liquids, gels, or solids. Other liquid or gel products are also encompassed such as, for example, gels such as, for example, shaving creams, and liquids such as, for example, foaming face washes. Although such products may be opaque, preferred products are non-opaque, i.e., transparent or translucent.

The fatty acids useful in the compositions of the present invention are preferably saturated fatty acids which are either linear or branched. Saturated fatty acids are preferred because they impart better color stability to soaps than do unsaturated fatty acids.

Single fatty acids or mixtures of two or more fatty acids may be used. Preferred fatty acids are $C_{12}$–$C_{20}$ fatty acids. Examples of such fatty acids include, but are not limited to, vegetable-derived fatty acids such as lauric acid, myristic acid, palmitic acid, stearic acid, and isostearic acid. One non-limiting example of a mixture of fatty acids useful herein is a mixture, by weight, of about 4% $C_{12}$–$C_{14}$ fatty acid, about 46% $C_{16}$ fatty acid, about 49% $C_{18}$ fatty acid, and about 1% $C_{18\text{-}1}$ fatty acid mixture, based upon 100% total weight of fatty acids. Another non-limiting example is a mixture, by weight, of about 2.5% $C_{12}$–$C_{14}$ fatty acid, about 10% branched $C_{16}$ fatty acid, about 6% linear $C_{18}$ fatty acid, about 65% branched $C_{18}$ fatty acid, about 2% linear $C_{18}$ fatty acid, about 2.5% $C_{18-1}$ fatty acid, about 8% branched $C_{20}$ fatty acid, and about 4% $C_{22}$ fatty acid, based upon 100% total weight of fatty acids.

The fatty acid is formulated for use in the compositions of the present invention by neutralization with, for example, caustic soda, alkanolamine, or the like. A preferred alkanolamine is triethanolamine which is available as an 85%–95% solution. Combinations of neutralizing agents may be used, and neutralization by a dual alkali system is preferred. Excess triethanolamine can be added to enhance transparency. Such an excess amount is typically a clarity enhancing effective amount.

Phenolic compounds are phenol group-containing compounds, and those useful herein include, but are not limited to, phenolic anti-microbial agents such as, for example, Triclosan; phenolic hydroxyacids such as, for example, salicylic acid; and salts of such acids. Triclosan is 5-chloro-2-(2,4-dichlorophenoxy) phenol. Triclosan is particularly photolabile in alkaline-based formulations and degrades upon exposure to sunlight. This is manifested by a yellowing in color. The initial products of photodegradation may be subject to secondary photolytic reactions or oxidation, which leads to color formation. The absorption spectra of Triclosan in various solvents are shown in FIG. 1. The spectrum of Triclosan in base solution is substantially the same as that in pure triethanolamine. Useful phenolic compounds also include, but are not limited to, phenolic compounds which are encapsulated by, for example, liposomes.

The amount of anti-microbial agent present in the soaps of the present invention may vary but is typically an anti-microbially effective amount. Preferred amounts of phenol group-containing compound(s) or anti-microbial agent(s) range, by weight, from about 0.1% to about 1% based upon 100% of the total weight of the composition.

Figure 2:
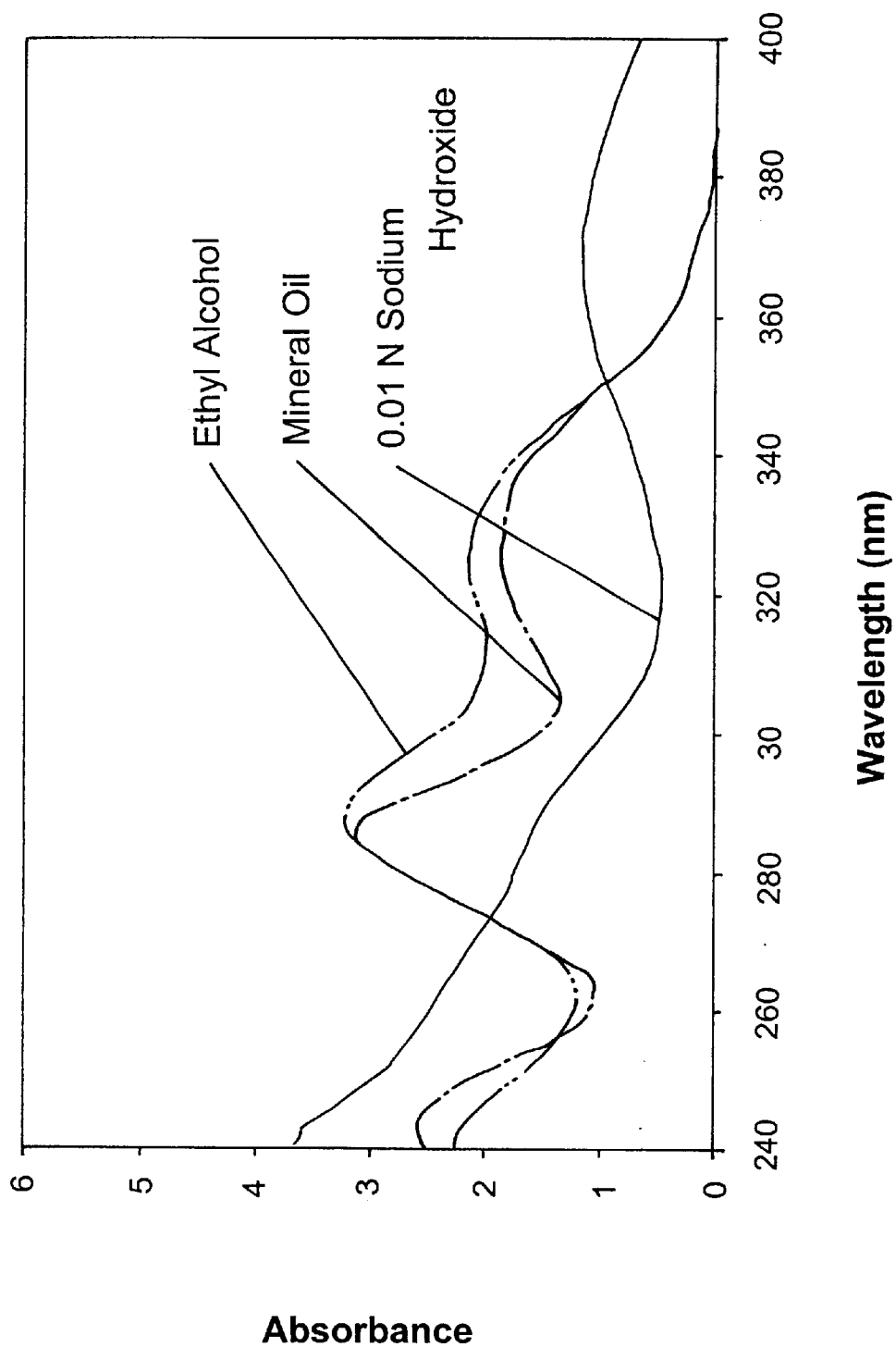
FIG. 2 is a graphic illustration of the UV absorption spectra of 50 ppm benzophenone-3 in ethyl alcohol, mineral oil, and 0.01N sodium hydroxide.

The UV absorbers of the compositions of the present invention improve the aesthetic appearance of the compositions and enhance the activity of the photolabile component. Photostable organic UV absorbers useful herein should not discolor when subjected to prolonged sunlight exposure. Further, the UV absorbers should encompass or include most of the absorption spectrum of the material being protected, which in the soaps described herein primarily are photolabile phenolic compounds. In general, the UV absorber should absorb both UV-B and UV-A components of solar radiation and should be either colorless or used in an amount sufficiently low that it does not impart any color to the product. Preferred UV absorbers are benzophenones, and particularly benzophenone-3, and octocrylene. The absorbent spectrum of benzophenone-3 is illustrated in FIG. 2 and overlaps that of Triclosan in a soap environment. Without being bound by any theory, it is believed that the UV absorber protects phenol group-containing compounds from UV degradation by competitively absorbing the energy of the UV-excited phenolic compounds. The UV absorber is typically present in a UV stabilizing effective amount, and preferably is present in an amount of less than or equal to about 1% by weight based upon 100% total weight of the composition. Most preferably, the amount of UV absorber, by weight, ranges from about 0.05% to about 0.25%, based upon 100% total weight of the composition. The weight ratio of UV absorber to phenol group-containing compounds typically ranges from about 1:10 to about 5:1 and preferably from about 1:10 to about 2:1. Most preferably, the range is from about 1:4 to 2:1. Most preferably, less UV absorber than phenol group-containing compounds, by weight, is present.

Additional components typically used in the preparation of such products may be added. Such additives include, but are not limited to, antioxidants, which may improve storage stability by preventing auto-oxidation. Auto-oxidation can result in rancidity which, in turn, can result in discoloration and malodor formation. A non-limiting example of a suitable antioxidant is alpha-tocopherol acetate. Other additives include, but are not limited to, humectants, such as glycerin; foam stabilizers, including, but not limited to, non-ionic foam stabilizers such as cocodiethanolamide; metal chelating agents including, but not limited to, disodium ethylene diamine tetra acetic acid (disodium EDTA); purified or deionized water; fragrances; colorants; or any combination of any of the foregoing.

The compounds of the present invention can be prepared by melting the fatty acid(s) at temperatures from about 55° C. to about 60° C. The melt may then be pretreated with sodium metal-sulfite to improve color. The resultant melt is then neutralized with alkaline, such as a preblended solution of triethanolamine and sodium hydroxide (50% solution), at appropriate stoichiometric proportions with excess of triethanolamine for transparency.

The phenol group-containing compound(s) and UV absorber(s) are then added. Additives such as glycerin, DTPA, foam stabilizers, fragrances, colorants, water, antioxidants, and the like are also added as soon as neutralization is complete.

The molten composition is then hot-poured into suitable trays and allowed to cool at ambient temperatures. When the desired bar hardening is achieved, the bars are cut, stamped and wrapped.

DESCRIPTION OF THE PREFERRED EMBODIMENTS

The following examples illustrate the invention without limitation.

EXAMPLES 1 AND 2 AND COMPARATIVE EXAMPLE 1A

Three base clear soap mixtures were prepared from the mixture of Table 1 below using a Caframo (Model R2R50) mixer and a hot plate for heating.

TABLE 1

| Fatty Acid | % by Weight Based upon 100% Total Weight of Fatty Acids |
|---|---|
| Lauric Acid | 13.61 |
| Myristic Acid | 6.63 |
| Palmitic Acid | 8.90 |
| Stearic Acid | 8.90 |
| Isostearic Acid | 4.19 |
| Sodium Hydroxide | 4.17 |
| Triethanolamine | 40.48 |
| Glycerin | 1.00 |
| Coconut Diethanolamide | 1.00 |
| EDTA | 0.16 |
| Fragrance RB 1001 | 0.20 |
| Water | q.s. |

Either 0.25% Triclosan and 0.1% benzophenone-3 (Example 1); 0.25% Triclosan and 0.05% benzophenone-3 (Example 2); or 0.25% Triclosan and 0% benzophenone-3 (Comparative Example 1A) were added to one of the three base soaps.

Figure 3:
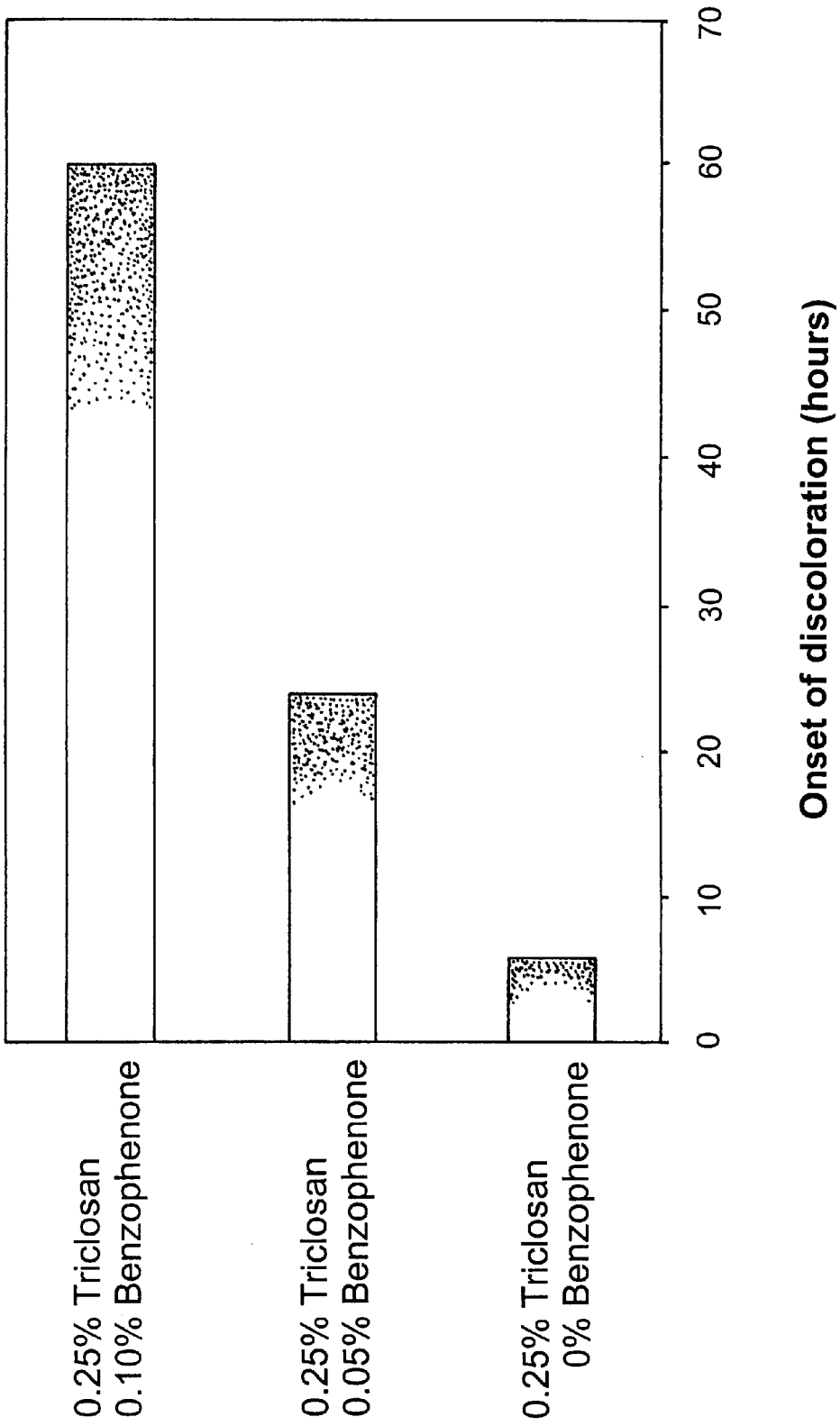
FIG. 3 is a graphic illustration of the effect of benzophenone-3 levels on discoloration from direct sunlight exposure.

Sunlight exposure tests were conducted under direct sunlight from 8 a.m. to 4 p.m. daily, and observations were made every hour. Results are illustrated as FIG. 3.

Figure 4:
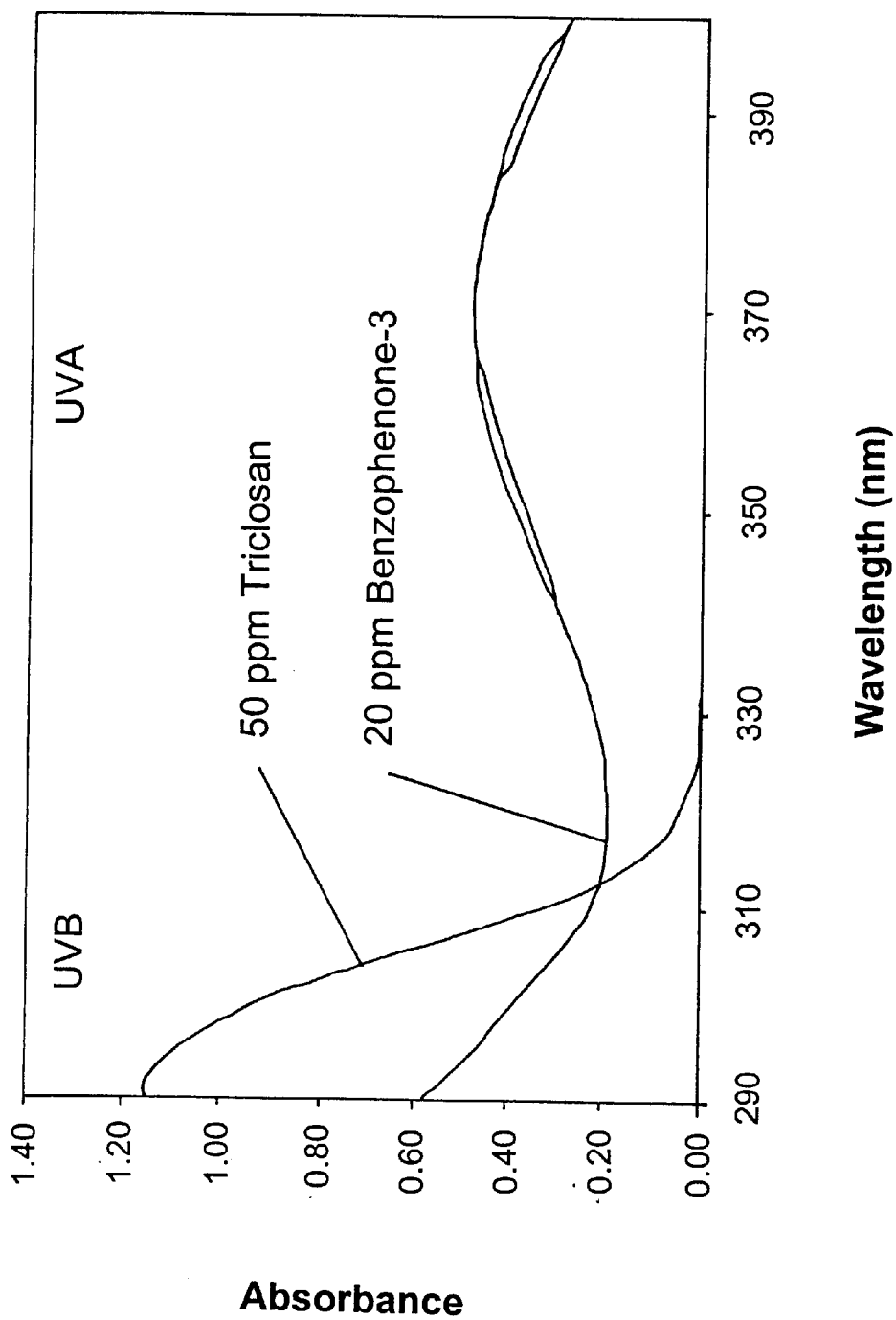
FIG. 4 is a graphic illustration of a comparison of the UV absorption spectra of 50 ppm Triclosan and 20 ppm benzophenone-3 in 0.01N sodium hydroxide.

The ultra-violet spectra of a 1:2.5 weight ratio of benzophenone-3 to Triclosan was obtained using a Perkin Elmer Lambda 2 spectrophotometer using quartz cavettes. Results are illustrated in FIG. 4.

EXAMPLE 3 AND COMPARATIVE EXAMPLE 3A

Two base clear soap mixtures were prepared as in Example 1. Either 0.25% sodium salicylate and 0.1% benzophenone-3 (Example 3) or 0.25% sodium salicylate (Comparative Example 3A) were added to the base soaps.

Sunlight exposure tests were conducted in Example 1. The soap containing the combination of sodium salicylate and benzophenone-3 remained clear after 10 hours of exposure to sunlight, while the soap containing sodium salicylate but without benzophenone-3 yellowed after 10 hours of exposure to sunlight.

Figure 5:
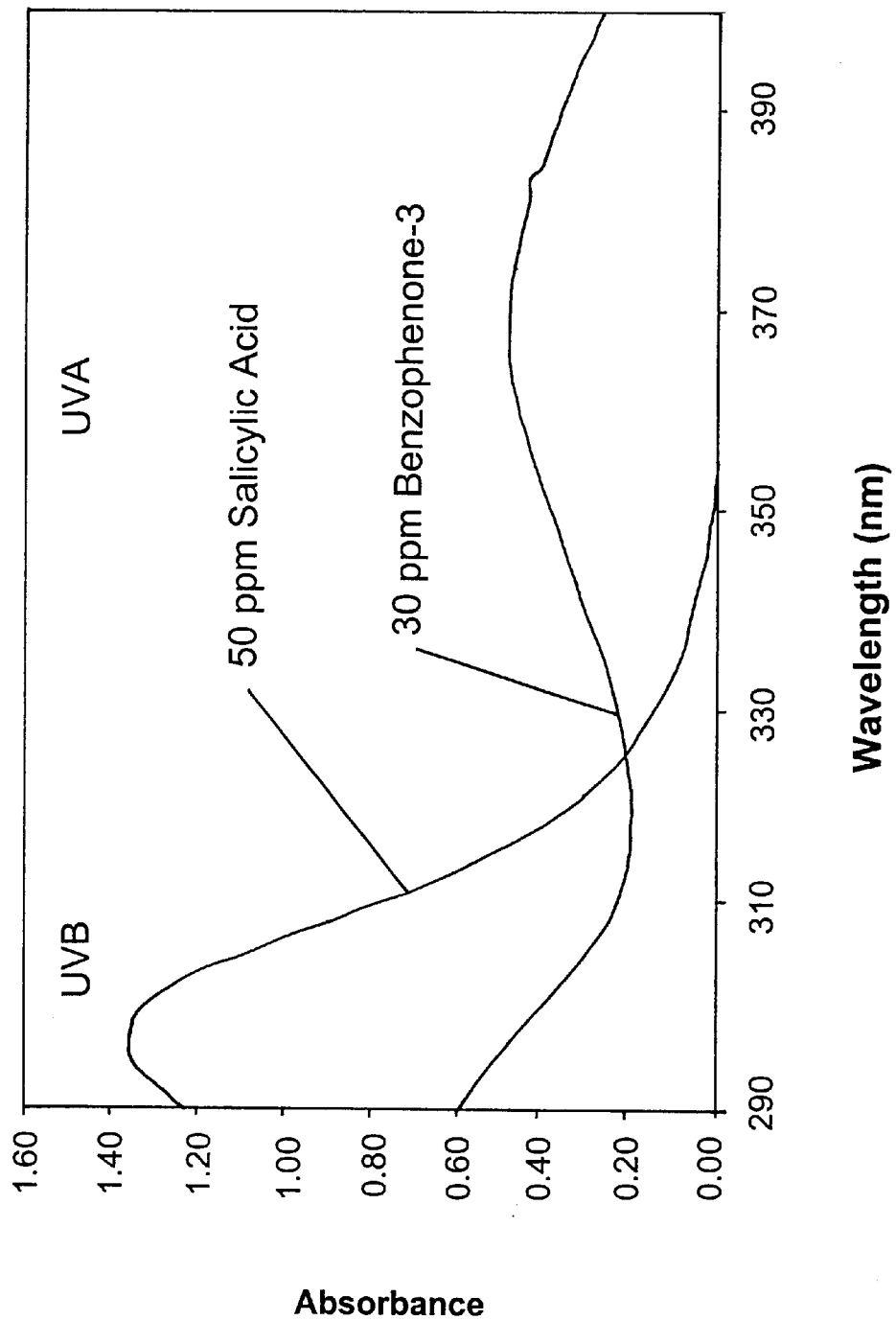
FIG. 5 is a graphic illustration of a compound of the UV absorption spectra of 50 ppm salicylic acid at 29 ppm benzophenone-3 in 0.01N sodium hydroxide.

The ultra-violet spectra of a 2:5 weight ratio of benzophenone-3 to salicylic and was obtained by the method described in Example 1. Results are illustrated in FIG. 5.

EXAMPLE 4

A mixture of fatty acids as shown in Table 2 below, is melted at a temperature between 55° C. and 65° C.

TABLE 2

| Fatty Acid | % by Weight Based upon 100% Total Weight of Fatty Acids |
|---|---|
| $C_{12}$–$C_{14}$ | 2.5 |
| $C_{16}$ Branched | 10 |
| $C_{16}$ Linear | 6 |
| $C_{10}$ Branched | 65 |
| $C_{18}$ Linear | 2 |
| $C_{18-1}$ | 2.5 |
| $C_{20}$ Branched | 8 |
| $C_{22}$ | 4 |

Sodium metabisulfite is added to the melt. The melt is then neutralized with a solution of triethanolamine and sodium hydroxide with an excess of triethanolamine. Triclosan and benzophenone-3 are added after neutralization.

The melt is hot poured into molds and is allowed to cool to a solid transparent bar.

EXAMPLE 5

The method of Example 4 is followed substituting the fatty acid mixture shown in Table 3 below, for the fatty acid mixture of Table 2.

TABLE 3

| Fatty Acid | % by Weight Based upon 100% Total Weight of Fatty Acids |
|---|---|
| $C_{12}$–$C_{14}$ | 4 |
| $C_{18}$ | 46 |
| $C_{18}$ | 49 |
| $C_{18-1}$ | 1 |

All patents, publications, applications, and test methods mentioned above are hereby incorporated by reference.

Many variations of the present invention will suggest themselves to those skilled in the art in light of the above, detailed description. All such obvious variations are within the patented scope of the appended claims.

We claim:

1. A fatty acid-based composition comprising:
    (a) at least one neutralized fatty acid;
    (b) a phenol group-containing compound;
    (c) cocodiethanolamide; and
    (d) a photostable organic ultra-violet absorber;
    wherein the weight ratio of said UV absorbent to said phenol group-containing compound ranges from about 1:10 to about 5:1.

2. A composition as defined in claim 1, wherein said fatty acid is selected from the group consisting of a $C_{12}$–$C_{20}$ linear fatty acid, a $C_{11}$–$C_{20}$ branched fatty acid, or any combination thereof.

3. A composition as defined in claim 2, wherein said fatty acid is selected from the group consisting of lauric acid, myristic acid, palmitic acid, stearic acid, isostearic acid, or any combination of any of the foregoing.

4. A composition as defined in claim 1, wherein said phenol group-containing compound comprises an anti-microbial agent.

5. A composition as defined in claim 4, wherein said anti-microbial agent is Triclosan.

6. A composition as defined in claim 1, wherein said ultra-violet absorbent absorbs both UV-A radiation and UV-B radiation.

7. A composition as defined in claim 6, wherein said ultra-violet absorbent is selected from the group consisting of benzophenones, octocrylene, or a combination thereof.

8. A composition as defined in claim 1, further comprising (d) an alkanolamine.

9. A composition as defined in claim 8, wherein said alkanolamine comprises triethanolamine.

10. A non-opaque, solid, anti-microbial soap comprising the composition of claim 1.

11. A translucent soap comprising the composition of claim 1.

12. A transparent soap comprising the composition of claim 1.

13. A composition as defined in claim 1, further comprising at least one component selected from the group consisting of:
    an antioxidant;
    a metal chelating agent;
    a humectant;
    a fragrance;
    a foam stabilizer;
    a colorant; and
    water.

14. A composition as defined in claim 1, wherein said ultra-violet absorber comprises less than or about 1% by weight of the total weight of said composition.

15. A composition as defined in claim 14, wherein said UV absorber comprises from about 0.05% by weight to about 0.25% by weight of the total weight of said composition.

16. A solid, non-opaque, anti-microbial soap comprising:
    (a) a neutralized mixture of saturated $C_{12}$–$C_{20}$ fatty acids;
    (b) triethanolamine;
    (c) Triclosan;
    (d) benzophenone-3; and
    (e) cocodie thanolamide.

17. A soap as defined in claim 16, further comprising:

(e) disodium EDTA:
(f) glycerin;
(g) an antioxidant;
(h) deionized water; and
(i) a fragrance.

18. A solid, non-opaque, anti-microbial soap comprising:
(a) a sodium hydroxide and triethanolamine neutralized mixture of saturated fatty acids, said fatty acid mixture comprising, by weight, about 2.5% $C_{12}$–$C_{14}$ fatty acids, about 10% $C_{16}$ branched fatty acid, about 6% $C_{16}$ linear fatty acid, about 65% $C_{18}$ branched fatty acid, about 2% $C_{18}$ linear fatty acid, about 2.5% $C_{18-1}$ fatty acid, about 8% $C_{20}$ branched fatty acid, and about 4% $C_{22}$ fatty acid, based upon 100% total weight of fatty acids;
(b) a transparency producing effective amount of triethanolamine;
(c) an anti-microbial effective amount of Triclosan; and
(d) a photostabilizing effective amount of benzophenone-3;
wherein the weight ratio of said benzophenone-3 to said Triclosan ranges from about 1:4 to about 2:1.

19. A method of preparing a fatty acid-based composition, said method comprising:
(a) melting a least one fatty acid at temperatures from about 55° C. to about 60° C.;
(b) neutralizing at least one melted fatty acid;
(c) adding an alkanolamine, a phenol group-containing compound, and a photostable organic UV absorber to said neutralized melted fatty acid to form a pourable composition; and
(d) cooling said pourable composition;
wherein the weight ration of said UV absorbent to said phenol group-containing compound ranges from about 1:10 to about 5:1.

20. A method as defined in claim 19, wherein step (b) of said method further includes adding a member selected from the group consisting of an anti-oxidant, a metal chelator, a humectant, a fragrance, a foam stabilizer, a colorant, water, or any combination of any of the foregoing.

* * * * *